(12) United States Patent
Froehlich

(10) Patent No.: US 8,241,340 B2
(45) Date of Patent: Aug. 14, 2012

(54) BONE ANCHOR SYSTEM

(75) Inventor: Markus Froehlich, Balterswil (CH)

(73) Assignee: Zimmer GmbH, Winterthur (CH)

( * ) Notice: Subject to any disclaimer, the term of this patent is extended or adjusted under 35 U.S.C. 154(b) by 2 days.

(21) Appl. No.: 12/876,568

(22) Filed: Sep. 7, 2010

(65) Prior Publication Data
US 2010/0331898 A1    Dec. 30, 2010

Related U.S. Application Data

(63) Continuation of application No. 11/870,978, filed on Oct. 11, 2007, now Pat. No. 7,789,901.

(51) Int. Cl.
*A61B 17/04*    (2006.01)
*A61B 17/86*    (2006.01)
*A61F 2/08*    (2006.01)

(52) U.S. Cl. .................. 606/302; 606/300; 606/305

(58) Field of Classification Search .............. 606/246, 606/265–267, 300–321, 73
See application file for complete search history.

(56) References Cited

U.S. PATENT DOCUMENTS

| 4,627,434 A | 12/1986 | Murray |
|---|---|---|
| 6,554,830 B1 | 4/2003 | Chappius |
| 7,128,743 B2 | 10/2006 | Metz-Stavenhagen |
| 2006/0161164 A1 | 7/2006 | Hwang et al. |
| 2007/0270858 A1* | 11/2007 | Trieu et al. ............... 606/73 |
| 2010/0016905 A1 | 1/2010 | Greenhalgh et al. |

FOREIGN PATENT DOCUMENTS

| DE | 19514758 A | 10/1996 |
|---|---|---|
| EP | 1132051 A | 9/2001 |
| WO | 200154598 A | 8/2001 |
| WO | 2004043303 A | 5/2004 |
| WO | 2006116760 A | 11/2006 |
| WO | 2007067857 A | 6/2007 |

\* cited by examiner

*Primary Examiner* — Eduardo C Robert
*Assistant Examiner* — Christina Negrelli
(74) *Attorney, Agent, or Firm* — Seager Tufte & Wickhem LLC

(57) ABSTRACT

A bone anchor system anchors a support member to a bone. The bone anchor system comprises a body having a shank adapted for insertion into a hole in the bone. A head is formed on the shank. The head has a support engagement portion adapted to secure the support member to the body. A passage extends from an entry point to an exit point formed in the body. An expandable member has a flexible wall at least partially enclosing an anchoring chamber. The expandable member has an expanded state configured to conform to a cavity in the bone. The anchoring chamber is in fluid communication with the exit point. The expandable member is adapted to expand when a filler material is provided into the anchoring chamber. A portion of the expandable member conforms to the cavity and the body and the support member are substantially anchored to the bone.

18 Claims, 6 Drawing Sheets

BONE ANCHOR SYSTEM

RELATED APPLICATION

This application is a continuation of U.S. patent application Ser. No. 11/870,978, filed on Oct. 11, 2007, now U.S. Pat. No. 7,789,901 the entire disclosure of which is incorporated herein by reference.

FIELD OF THE INVENTION

This invention relates to surgical anchors for securing support members to bone, and more particularly, to bone anchor systems for securing a support member to a vertebra.

BACKGROUND OF THE INVENTION

Skeletal structures are formed of bones and adjoining structures which include cartilage, for instance. These skeletal structures may require artificial support or stabilization. For example, the human spine is composed of a column of thirty-three bones, called vertebrae, and their adjoining structures. Most of the vertebrae are capable of individual movement and generally are connected by anterior and posterior longitudinal ligaments. An intervertebral disc is positioned between opposing faces of adjacent vertebrae. Each of these vertebrae include a vertebral body and a dorsal-arch that enclose an opening, called the vertebral foramen, through which the spinal cord and spinal nerves pass. Unfortunately, there are numerous diseases that deteriorate one or more portions of the vertebra or disc. As a result, nerves may be pinched causing enormous pain. In these and other situations, surgical installation of various devices is designed to reduce pain to allow the person to resume a normal life.

One well-known device for spine stabilization procedures is the pedicle screw which is threaded for engagement with bone. A pedicle screw is surgically installed posteriorly into and through a pedicle. A support member such as a plate, semi-rigid member, flexible member, or rigid rod is attached to the pedicle screw for stabilization of the spine. If the threaded portion of the screws do not properly secure to the bone, the pedicle screw will loosen and pull out or break. This loosening can occur over time. Securing the pedicle screw is even more problematic when the bone, particularly cancellous bone, is diseased, deteriorating, or degenerating. For instance, when a pedicle screw is used on osteoporotic patients, the lack of bone density makes it difficult to properly engage the pedicle screw threads within the pedicle resulting in a fragile connection between the pedicle screw and bone.

Therefore, a bone anchor system with improved fixation to bone that does not require screwing into bone and where the external load is dispersed to other load bearing structures in contact with bone is needed.

SUMMARY OF THE INVENTION

The invention provides a bone anchor system for anchoring a support member to a bone. The bone has a hole formed therein and a cavity formed at a distal end of the hole. The bone anchor system comprises a body having a shank that has a proximal portion and a distal portion adapted for insertion into the hole. A head is formed on the proximal portion of the shank, and has a support engagement portion adapted to secure the support member to the body. A passage extends from an entry point formed at the proximal portion to an exit point formed in the distal portion. The bone anchor system further comprises an expandable member having a flexible wall at least partially enclosing an anchoring chamber, and an expanded state configured to conform to the cavity. The distal portion of the shank cooperates with the expandable member and the anchoring chamber is in fluid communication with the exit point. The expandable member is adapted to expand when a filler material is provided into the entry point, passes through the passage, passes out of the exit point, and into the anchoring chamber. Upon filling the anchoring chamber with the filler material, a portion of the expandable member conforms to the cavity and the body and the support member are substantially anchored to the bone.

The invention further includes a method for securing a support member to a bone. The method comprises forming a hole in the bone, removing additional bone at a distal end of the hole to form a cavity, inserting the bone anchor system into the hole, and providing a filler material into the entry point to the anchoring chamber to fill and thereby expand the anchoring chamber of the expandable member within the cavity. Upon filling the anchoring chamber with the filler material, a portion of the expandable member conforms to the cavity, and the body and the support member secured thereto are substantially anchored to the bone. [0007] In another embodiment, the bone anchor system includes a first body and a second body, each having the shank, the head, and the passage, and the expandable member is a tubular member having a first opening, a second opening, and the anchoring chamber therebetween. For this embodiment, the method comprises forming a first hole through a first pedicle into a vertebra, forming a second hole in a second pedicle into the vertebra, and then removing additional bone to form a cavity connecting the first hole with the second hole. The second opening of the tubular member is inserted into the first hole, through the cavity, and out of the second hole to position the first opening adjacent the first hole, the second opening adjacent the second hole, and the anchoring chamber within the cavity. The shank of the first body is inserted into the first opening of the tubular member and into the first hole. The shank of the second body is inserted into the second opening of the tubular member and the second hole. The filler material is provided to at least one of the passages of the first and second bodies and into the anchoring chamber to fill and thereby expand the anchoring chamber of the tubular member within the cavity. Upon filling the anchoring chamber with the filler material, a portion of the expandable member conforms to the cavity and the first body, the second body and the support member secured therebetween are substantially anchored to the vertebra.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
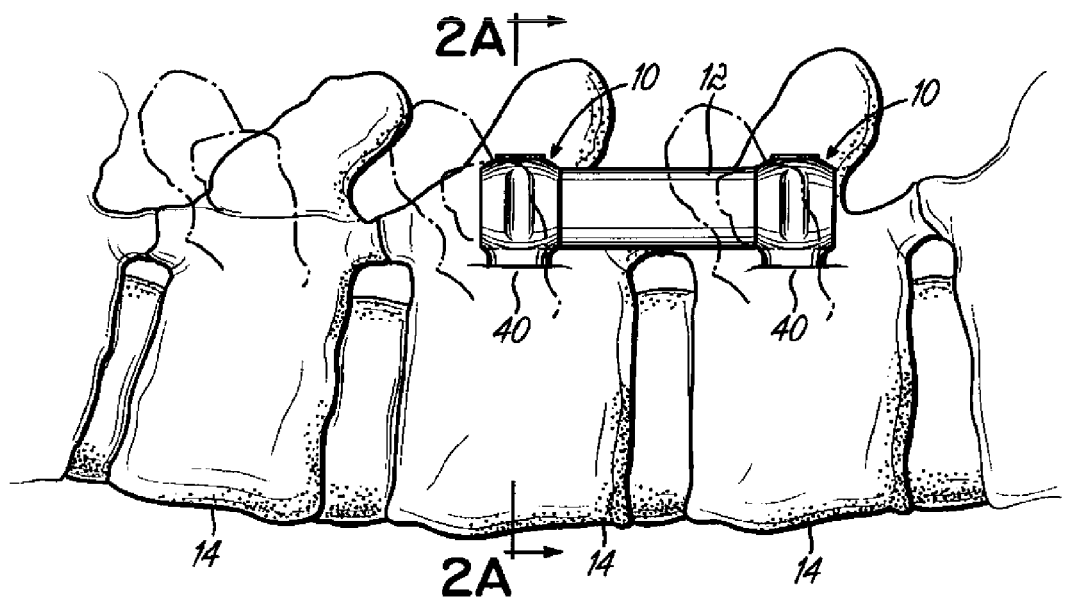
FIG. 1 is side elevation view of a spine having two bone anchor systems inserted into adjacent vertebra with a support member secured at each end by the adjacent bone anchor systems.
Figure 2A:
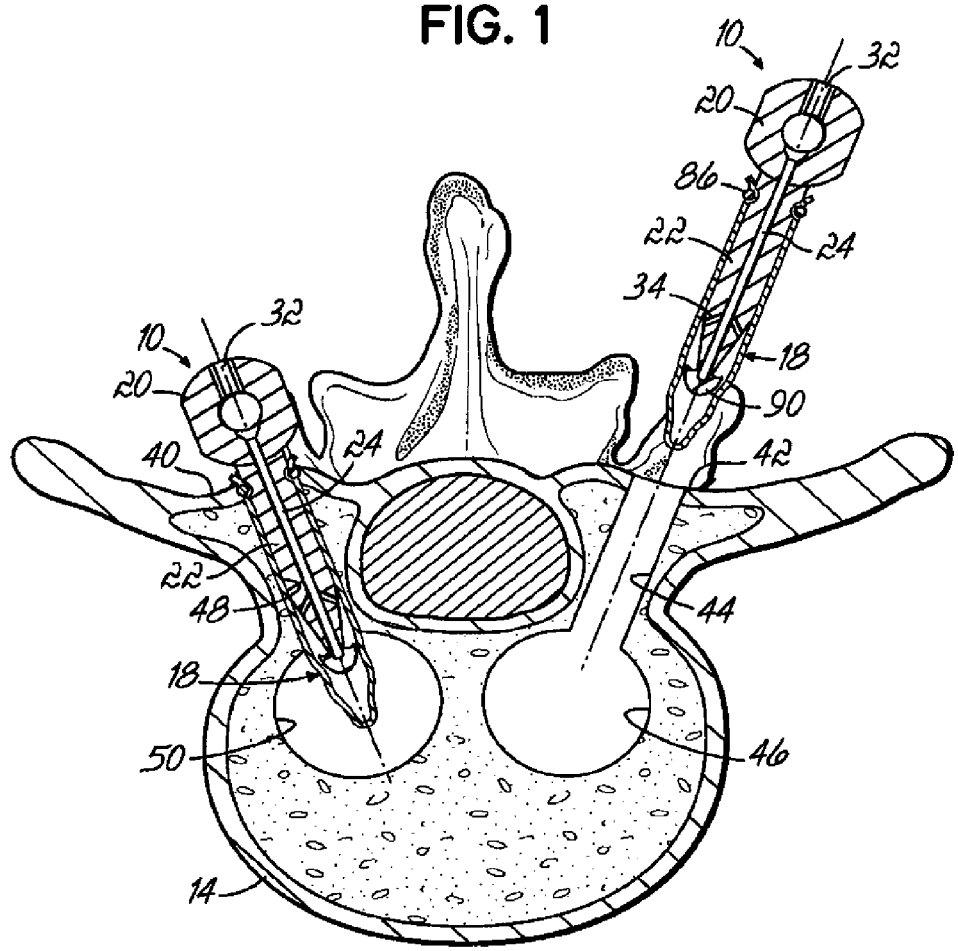
FIGS. 2A and 2B are cross-sectional views of the spine of FIG. 1 taken along section line 2A-2A, showing one embodiment of the bone anchor system having an expandable member in an unexpanded state and in an expanded state, respectively, inserted into both the first and second pedicles.
Figure 2B:
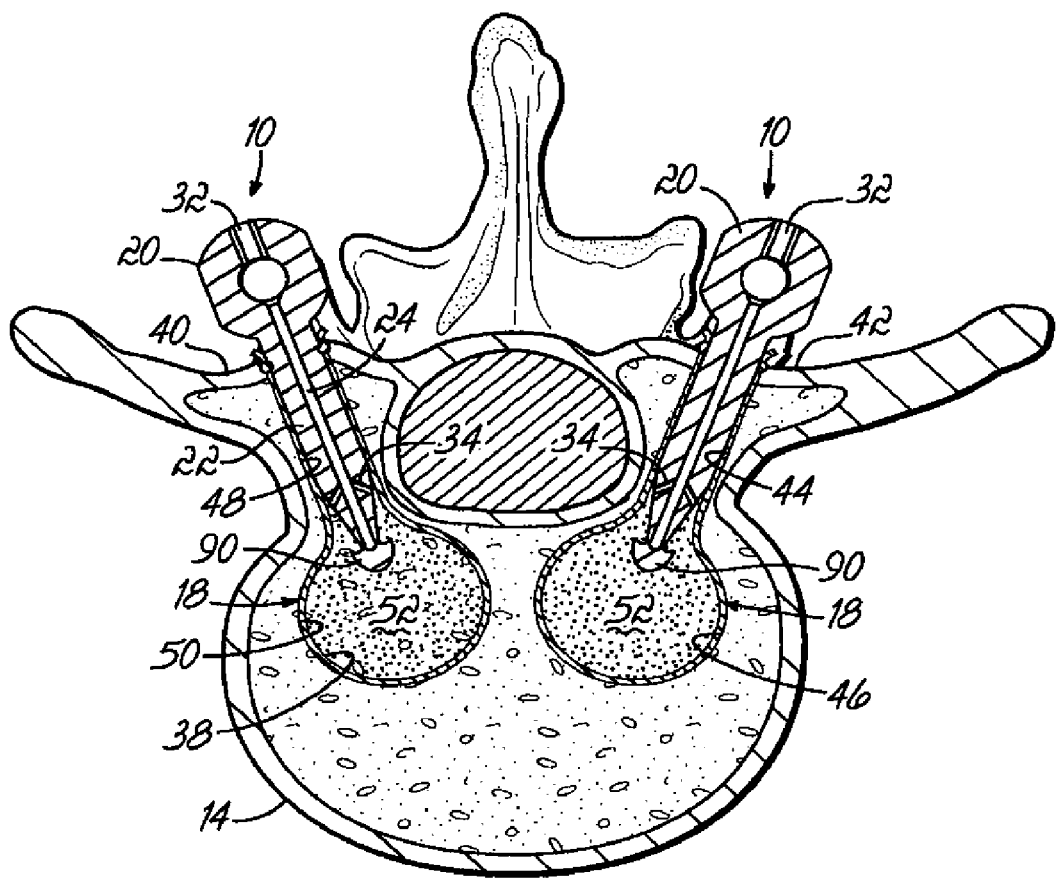
Figure 3:
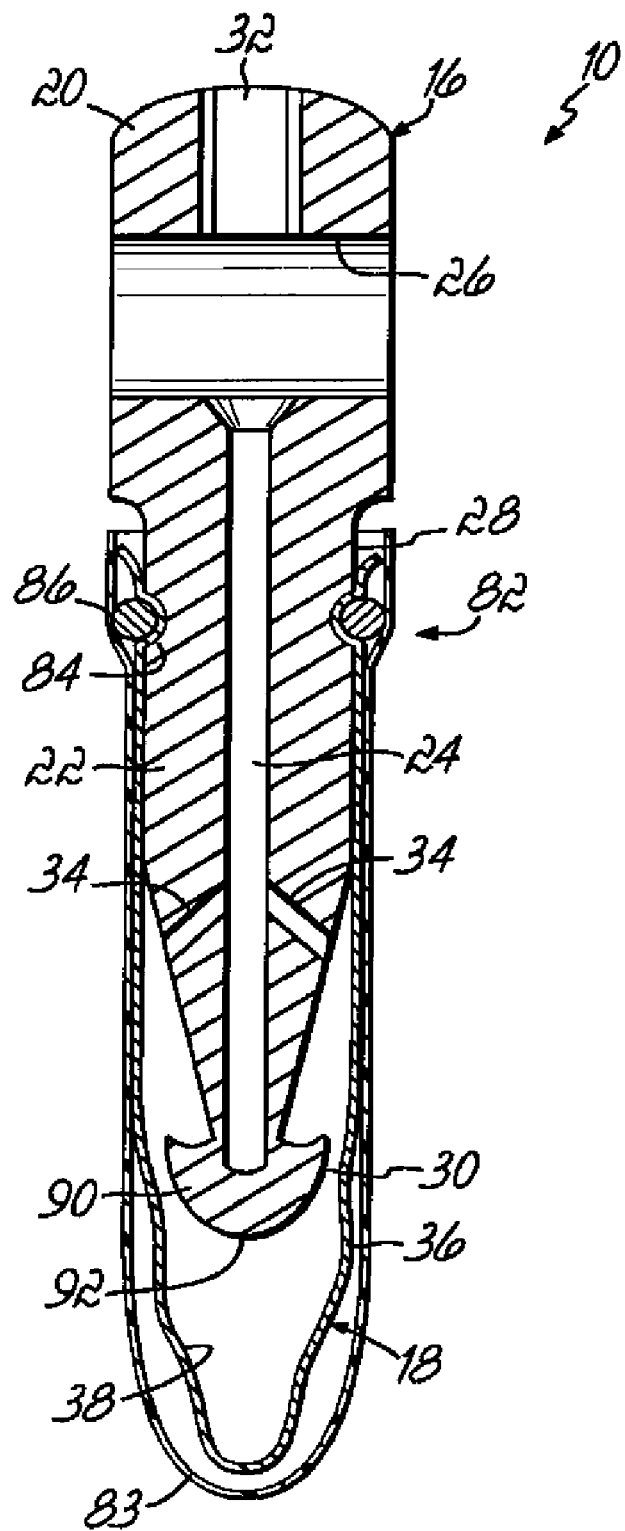
FIG. 3 is a cross-sectional view of one embodiment of the bone anchor system with the expandable member in an unexpanded state.

FIGS. 1-3 depict an exemplary bone anchor system 10 according to the principles of the present disclosure. The bone anchor system 10 facilitates anchoring a support member 12 to a bone 14. In one embodiment, as shown in FIG. 1, two bone anchor systems 10 secure the support member 12 between adjacent vertebral bodies 14. By way of example, the support member 12 may be a combination of spacer, for instance SULENE®-PCU, and cord, for instance SULENE®-PET, that is currently a part of the DYNESYS® Dynamic Stabilization System available from Zimmer Spine, Edina, Minn. In other applications, the support member 12 may be a rigid member such as a rod or a plate, a semirigid member, a flexible member, or another member adapted to be anchored to bone.

While the embodiments illustrated in the figures depict the bone anchor system 10 for anchoring the support member 12 to a vertebral body 14, one skilled in the art will observe that the bone anchor system 10 may be used to attach a variety of other support members to other bones, in both humans and nonhumans. Due to its configuration, subsequent loading of the support member 12 may not loosen or break the bone anchor system 10 as is known with prior art threaded bone anchors, pedicles screws and the like. Additionally, the construction of the bone anchor system 10 can conform to a void existing within the bone 14. This void may be preexisting in bone-like osteoporotic bone or created by a surgeon as described below. Furthermore, the bone anchor system 10 can be easier to install. In one exemplary embodiment as shown, for example, in FIG. 2A, the bone anchor system 10 does not require screwing a device into the bone 14. Yet, in contrast with the prior art, the bone anchor system 10 can be implanted directly into a hole created in the pedicle, can provide greater stability, and may provide improved fixation of the support member 12 to the bone 14.

With reference to FIG. 3, the bone anchor system 10 includes a body 16 and an expandable member 18. The body 16 has a head 20, a shank 22, and a passage 24. The head 20 has a support engagement region 26 for securing the support member 12 to the body 16. The support engagement region 26 may be, for instance, similar to a polyaxial top-loading head, known in the art. The shank 22 has a proximal portion 28 proximate to the head 20 and a distal portion 30 opposite the head 20. The passage 24 extends from an entry point 32 formed in the head 20, through the shank 22, and exits at an exit point 34 in the distal portion 30. Although FIG. 3 illustrates the passage 24 in the center of the shank 22, the passage 24 may be a channel or passage along the outer surface that can receive a filler material via a delivery tube (not shown). By way of example and not limitation, the body 16 may be made of titanium or one of its alloys, stainless steel, TRABECULAR METAL™ material sold by Zimmer Spine, Inc. of Edina, Minn., or other biocompatible material suitable for biological use.

The expandable member 18, as shown in FIG. 3 in an unexpanded state, cooperates with the shank 22. In one embodiment, the expandable member 18 matches the profile of the body 16 to aid in insertion into bone. The expandable member 18 has a flexible wall 36 that at least partially encloses an anchoring chamber 38. Therefore, the anchoring chamber 38 is in fluid communication with the passage 24. By way of example, the expandable member 18 may be a metallic, woven fabric made of titanium or one of its alloys, stainless steel; a polymeric material, such as polymethyl methacrylate (PMMA); or other biologically compatible metals suitable for biological use. In one embodiment, the expandable member 18 may be a conforming member that conforms to the shape of a void in bone.

FIGS. 2A and 2B depict an exemplary embodiment of a pair of bone anchor systems 10, for example, one bone anchor system 10 for anchoring to a first pedicle 40 and a second for anchoring to a second pedicle 42. In FIG. 2A, each of the expandable members 18 is shown in an unexpanded state with one bone anchor system 10 shown prior to insertion into a hole 44 formed in the vertebral body 14 with a cavity 46 formed at a distal end of the hole 44. To further illustrate the placement of the bone anchor system 10 in the bone 14, a second bone anchor system 10 is also shown in FIG. 2A. The second bone anchor system 10 is positioned in a second hole 48 and a second cavity 50 has been formed at the distal end of the second hole 48. While two bone anchor systems 10 are shown and described, a single bone anchor system 10 may be used to secure the support member 12 to the bone 14. In FIG. 2A each of the bone anchor systems 10 are inserted into their respective holes 44, 48 without relative rotation, i.e. no screwing is required. As will be describe in more detail later, in an alternative embodiment, a portion of the body 16 can include threads at the proximal portion 28 of the shank 22 designed to engage the pedicle 40, with the distal portion 30 being free of threads. In yet another alternative embodiment, a portion of the body 16 can include generally longitudinally formed projections or ribs that engage the pedicle 40 possibly stabilizing the body 16 against torque.

The holes 44, 48 may be formed by hand with a tool or machined, such as by drilling with a drill, into the bone 14 or by other methods known in the art. The cavities 46, 50 may also be formed by similar methods. In one exemplary embodiment, at least one dimension of each cavity 46, 50 is larger than the diameter of the respective hole 44, 48.

Now with reference to FIG. 2B, the expandable members 18 of each bone anchor system 10 are shown in an expanded state. In accordance with the principles of the present disclosure, following insertion of the bone anchor system 10 into the hole 44, as described previously and shown in the FIG. 2A, a filler material 52 is provided into the passage 24. The filler material 52 passes through the passage 24 into the anchoring chamber 38 to expand the expandable member 18. As the anchoring chamber 38 fills, for example, by injecting the filler material 52 therein, the flexible wall 36 may contact the surface of the cavity 46. While the expandable member 18 may be entirely filled with the filler material 52 such that the flexible wall 36 conforms to the cavity 46, it will be appreciated that partially filling the anchoring chamber 38 may also facilitate fixation of the bone anchor system 10 to the bone 14. By way of example and not limitation, the filler material 52 may include bone cement or in situ curable polymeric materials including, for example, elongated polymeric materials, polymeric beads, hydrogel materials, fusion promoting materials, autograft bone, allograft bone, xenograft bone, or any combination thereof. Furthermore, other desired materials including bioresorbable materials, may include poly(lactic acid), poly(glycolic acid), p-dioxanon fibers, polyarylethyl, polymethyl methacrylate, polyurethane, amino-acid-derived polycarbonate, polycaprolactone, aliphatic polyesters, calcium phosphate, unsaturated linear polyesters, vinyl pyrrolidone, polypropylene fumarate diacrylate, or mixtures thereof, or other biocompatible compounds.

In an exemplary embodiment, a flowable and curable filler material 52 fills and expands the expandable member 18 and hardens in vivo. As shown in FIG. 2B, once the expandable member 18 is expanded such that one of its dimensions is greater than a diameter of the hole 44, for example, the expandable member 18 will have an interference fit with the hole 44 and can conform to the cavity 46. Thus, the expandable member 18 will resist loads that act to pull the body 16 longitudinally from the hole 44 by transferring those loads to the bone 14 over a larger area than prior art bone anchors, pedicle screws and the like. For similar reasons, the bone anchor system 10 also resists lateral forces that may act to loosen it to a greater degree than prior art devices. While FIGS. 2A and 2B depict the cavities 46, 50 having a generally circular cross section, one skilled in the art will observe that the cavities 46, 50 may have a variety of shapes and sizes. In any case, when the filler material 52 expands the expandable member 18, the expandable member 18 may conform to the cavity 46 with the flexible wall 36 abutting the surface of the cavity 46 to create an interference fit between the expandable member 18 and the hole 44, as previously mentioned.

Figure 4A:
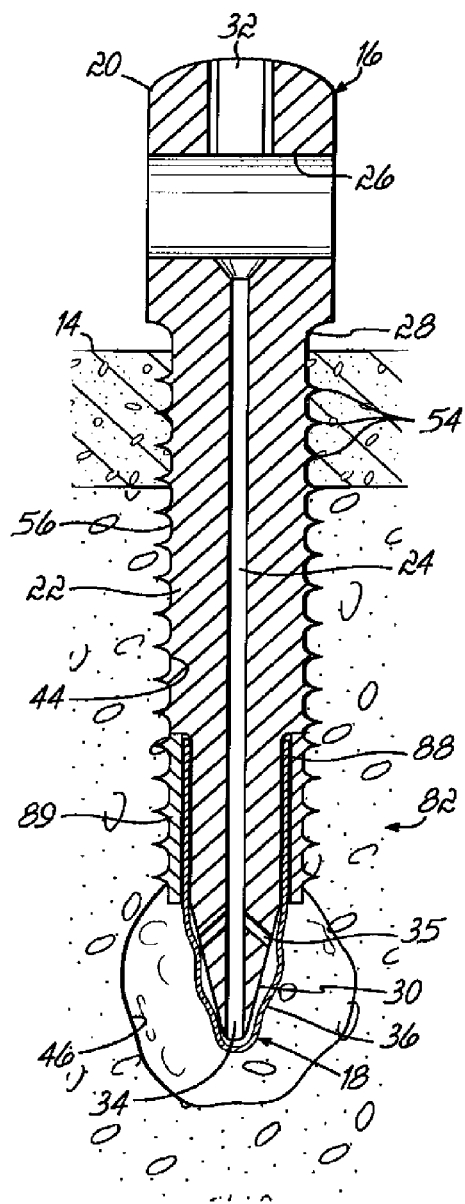
FIGS. 4A and 4B are cross-sectional views of another embodiment of the bone anchor system having a threaded portion in threaded engagement with bone with the expandable member in an unexpanded state and an expanded state, respectively.
Figure 4B:
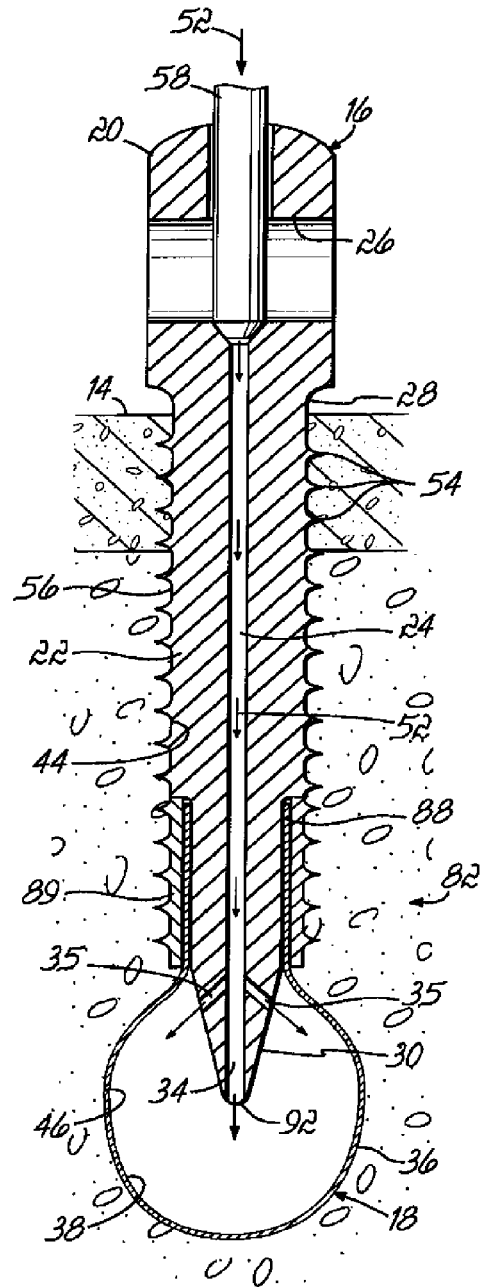

With reference now to FIGS. 4A and 4B, another exemplary embodiment of the bone anchor system 10 is depicted. As shown, the shank 22 has a helical thread 54 on a threaded portion 56 between the proximal portion 28 and the distal portion 30. Thus, the surgeon may screw the body 16 into the bone 14. The threaded portion 56 frictionally engages the bone 14 surrounding the hole 44 as the surgeon rotates the body 16. In addition, to further stabilize and support the body 16 and support member 12, the surgeon may introduce the filler material 52 into the expandable member 18, as shown in FIG. 4B. A cannula 58 may be inserted at least partially into the passage 24 to introduce the filler material 52 into the passage 24 to expand the expandable member 18 with the cavity 46. Once the filler material 52 is in the anchoring chamber 38, it may begin hardening. In this embodiment, the passage 24 can be used as a cannulated delivery mechanism in conjunction with a guide wire (not shown) for percutaneous delivery of the bone anchor system 10. In another embodiment, a wire can be inserted in the passage 24 to engage the expandable member 18 and maintain the expandable member 18 in a configuration that allows for filling with the filler material 52.

Figure 5:
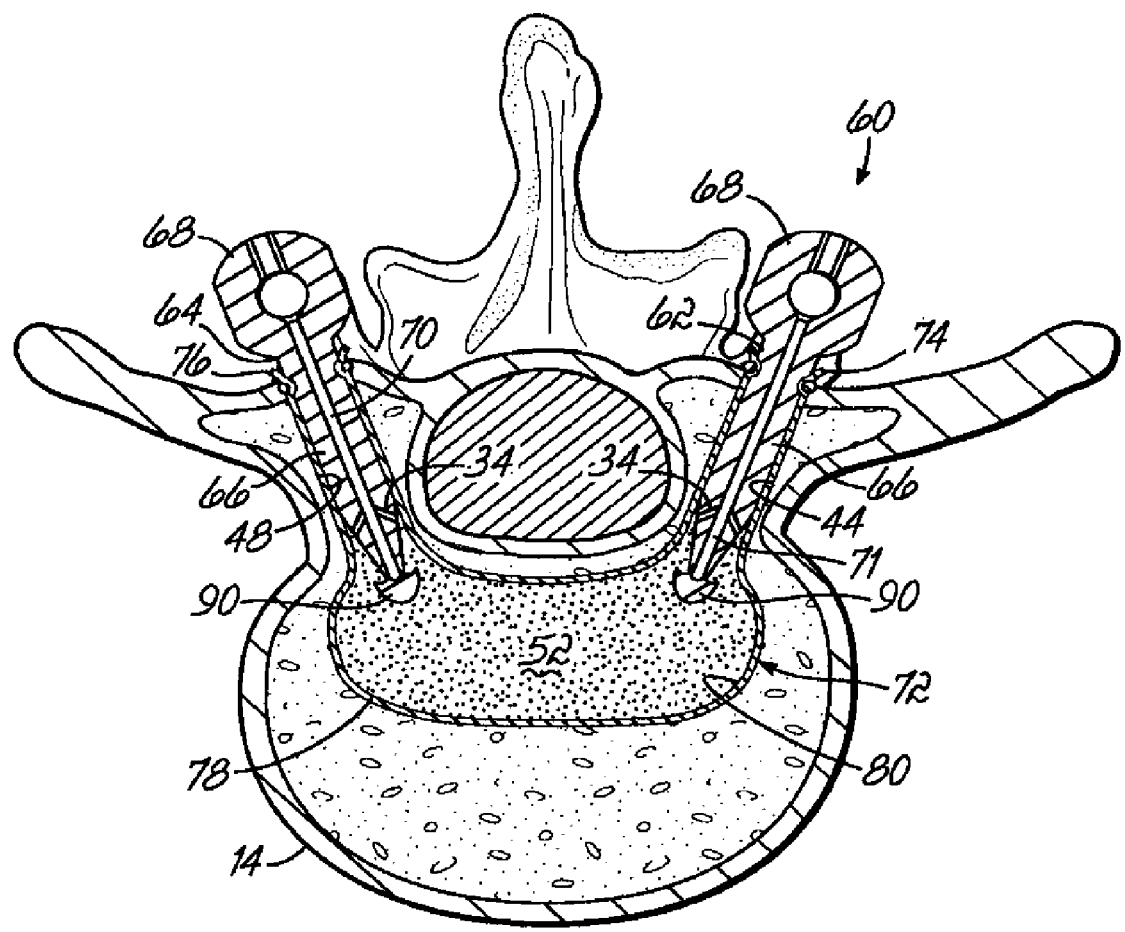
FIG. 5 is a cross-sectional view of the spine of FIG. 1 taken along section line 2A-2A, showing another embodiment of the bone anchor system having an expandable member in an expanded state.

In another exemplary embodiment, as shown in FIG. 5, a bone anchor system 60 includes a first body 62 and a second body 64. Each of the bodies 62, 64 may be similar such that they each have a shank 66, a head 68, and a passage 70. Alternatively, only one of the bodies 62, 64 may include a passage 70. An expandable member 72 cooperates with both the first and the second bodies 62, 64 through a first and second openings 74, 76 in a flexible wall 78. Thus, in one embodiment the expandable member 72 has a tubular configuration. The flexible wall 78 at least partially encloses an anchoring chamber 80. Once the expandable member 72 is inserted and at least partially filled, the anchoring chamber 80 may have, for example, a u-shape. The anchoring chamber 80 may prevent longitudinal withdrawal of either or both bodies 62, 64 from their respective holes 44, 48. As one skilled in the art will observe and appreciate, in addition to transferring loads to the bone 14 surrounding the expandable member 72, any loads acting to withdraw the bone anchor system 60 may be distributed to other portions of the bone anchor system 60, such as from the first body 62 to the second body 64 or vice versa.

Figure 6:
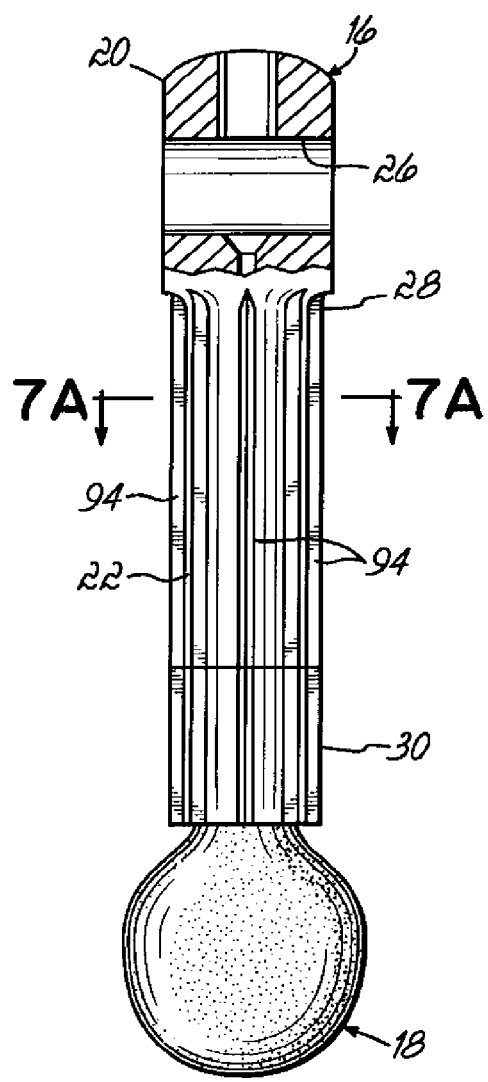
FIG. 6 is a partial cross-sectional view of another embodiment of the bone anchor system having a projection extending from the body for engagement with bone.
Figure 7A:
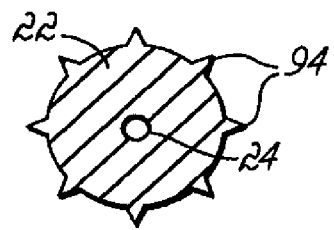
FIGS. 7A, 7B, and 7C are cross-sectional views of FIG. 6 taken along section line 7A-7A, showing other embodiments of the projection.
Figure 7B:
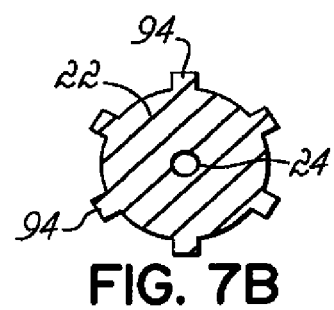
Figure 7C:
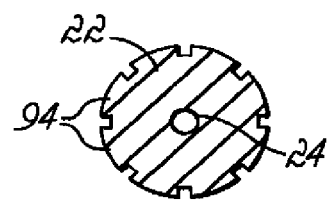

As previous mentioned and with reference now to FIGS. 6, 7A, 7B, and 7C, the body 16 may include one or more ribs or projections 94 extending therefrom. As shown in FIG. 6, the projections 94 are generally formed along the shank 22 between the proximal portion 28 and the distal portion 30 and project radially from the body 16. The projections 94 may sufficiently engage the bone 14 and thus prevent rotation of the body 16 therein when a torque is applied to the body 16 via the support engagement region 26, for example. While FIG. 6 depicts the projections 94 as extending along the shank 22 from the proximal portion 28 to proximate the distal portion 30, one skilled in the art will observe that even discrete (i.e. those extending less than the length of the shank 22) projections extending radially from the body 16 to engage the bone 14 may prevent rotation of the body 16. FIGS. 7A, 7B, and 7C are examples of cross sections of exemplary projections 94. It will be appreciated, however, that the projections 94 may have many other configurations.

As shown best in FIGS. 3, 4A, and 4B, in other exemplary embodiments, the expandable member 18 is secured to the shank 22 by a securing system 82 such as a clamping system. The securing system 82 may ease handling of the bone anchor system 10 by preventing the expandable member 18 from inadvertently falling off the shank 22 prior to insertion into the hole 44. Also, the securing system 82 may prevent the body 16 from being accidentally withdrawn from the expandable member 18 during or following inflation but prior to the filler material 52 hardening. Moreover, the securing system 82 may enhance the stability of the bone anchor system 10 by providing additional interfacial support between the body 16 and the expandable member 18 even after the filler material 52 has hardened. In one embodiment, a sheath 83 that is more rigid than the expandable member 18 can be provided over the expandable member 18 that maintains the shape and position of the expandable member 18 on the body 16. The sheath 83 may include a mechanism that allows removal of the sheath 83 after placement of the bone anchor system 10.

In an exemplary embodiment, as shown in FIG. 3, the securing system 82 may, for example, frictionally secure the expandable member 18 to the shank 22. In this embodiment, the shank 22 is formed with a recess 84. A compression ring 86, having generally the same shape as the recess 84, captures the flexible wall 36 within the recess 84. The ring 86 may be sized and shaped to apply compressive loads to the flexible wall 36 to enhance the frictional forces that secure the flexible wall 36 within the recess 84. In one embodiment, the compression ring 86 engages the shank 22 adjacent to the proximal portion 28 making the securing system 82 accessible after the body 16 is inserted into the bone 14.

FIGS. 4A and 4B illustrate another example of a securing system 82. In this embodiment, the threaded portion 56 has a longitudinal annular recess 88. The longitudinal annular recess 88 may be formed between a portion of the shank 22 and a sleeve 89 and extend from the distal portion 30 toward the proximal portion 28. The longitudinal annular recess 88 cooperates with the flexible wall 36 of the expandable member 18 such that the flexible wall 36 may be inserted into the longitudinal annular recess 88. For example, the flexible wall 36 may be placed around the shank 22 and the sleeve 89 may slide over the flexible wall 36 into a position proximate the shank 22 to clamp or otherwise frictionally engage the flexible wall 36. In addition, when the shank 22 is inserted into the bone 14, the threaded portion 56 threadably engages the bone 14, which may compress the sleeve 89 onto the flexible wall 36, thus clamping the expandable member 18 within the longitudinal annular recess 88. In another embodiment, the distal portion 30 may taper toward a distal end 92 to facilitate insertion of the bone anchor system 10 into the hole 44. As with the previously described securing system 82, the longitudinal annular recess 88 may prevent separation of the expandable member 18 from the body 16 before, during, and after expansion of the anchoring chamber 38, as well as, prior to hardening of the filler material 52.

With reference to FIG. 3, in another embodiment, the shank 22 is formed having a crown and fluke configuration 90. The crown and fluke configuration 90 are formed at the distal portion 30 of the shank 22. As shown in FIG. 2B, the crown and fluke configuration 90 submerge in the filler material 52 when the anchoring chamber 38 is filled with the filler material 52. In this embodiment, when the filler material 52 fully expands the expandable member 18, and in the use of an in situ curable filler material 52 that fully hardens, the crown and fluke configuration 90 facilitate capturing of the body 16 within the filler material 52 essentially anchoring the body 16 within the filler material 52 against loads tending to withdraw the body 16 from the bone 14. With reference to FIGS. 4A and 4B, in another embodiment, the exit point 34 is formed at the distal end 92 of the shank 22 and one or more other exit points 35 branch from the passage 24 in the distal portion 30 proximal to the distal end 92. It will be appreciated that when the expandable member 18 is filled to capacity with the filler material 52, and residual filler material 52 "backs up" into the exit point 34 and other exit points 35 and into the passage 24, the body 16 may be more rigidly secured against forces acting on the body 16 due to the additional contact surface area created by the exit points 34, 35 and the filler material 52.

In another exemplary embodiment, best shown in FIG. 3, the shank 22 is formed with the crown and fluke configuration 90 formed on the distal end 92, and the exit point 34 is formed proximal to the distal end 92. Thus, when the filler material 52 flows through the passage 24 and out the exit point 34, the filler material 52 may flow over and around the crown and fluke configuration 90. In an event where the expandable member 18 is less than fully expanded, or when the bone anchor system 10 is oriented such that the filler material 52 flows away from the distal portion 30, the filler material 52 will be more likely to remain in contact with the crown and fluke configuration 90 and, consequently, may be more likely that the filler material 52 may, in the case of an in situ curable filler material, hardens around the crown and fluke configuration 90. Thus, making it more likely that loads distributed to the body 16 will be transferred directly to the filler material 52 rather than from the body 16 to the expandable member 18 and then to the filler material 52.

Similar to the method of installing the bone anchor system 10 shown in FIGS. 2A and 2B, in another embodiment a method of securing a support member 12 to a bone 14 comprises forming the first and the second holes 44, 48 into the bone 14 such that the holes 44, 48 are in fluid communication, as shown only in FIG. 5. As one skilled in the art will appreciate, the holes 44, 48 may be formed whereby they intersect, or additional bone at the distal portion of the holes 44, 48 may be removed to connect the holes 44, 48. In any case, once two holes 44, 48 are connected, expandable member 72 may be inserted through one hole 44 and out the other 48. The first and second bodies 62, 64 are inserted into the first and second openings 74, 76 in an arrangement as shown in FIG. 5. It will be appreciated that the present disclosure is not limited to any particular order in which the first and second bodies 62, 64 is inserted into the bone 14. For instance, in one exemplary method, the expandable member 72 is inserted into one hole 44 and out of the second hole 48. Following insertion of the expandable member 72, the first opening 74 remains accessible in the first hole 44 and the second opening 76 remains accessible within the second hole 48. Therefore, the first and second bodies 62, 64 may be inserted into their respective openings 74, 76 and, consequently, into their respective holes 44, 48.

In another embodiment, one body 62 may be secured to the expandable member 72 between the recess 84 and the ring 86 of the securing system 82 of FIG. 3. One end of the expandable member 72 may then be inserted into the hole 44 followed by insertion of the body 62 into the hole 44. The other end of the expandable member 72 is pulled out of the second hole 48. At this point the expandable member 72 may be trimmed to length near the surface of the pedicle 40 prior to inserting the second body 64 into the second hole 48 and possibly clamping the expandable member 72 to the second body 64. One skilled in the art will observe that there are a number of different orders that the expandable member 72 and the first and second bodies 62, 64 may be inserted into their respective openings 74, 76 and holes 44, 48.

Once the expandable member 72 and the first and second bodies 62, 64 are inserted into the holes 44, 48, the filler material 52 may be provided to the expandable member 72 through the passage 70 or a second passage 71 and into the anchoring chamber 80. One skilled in the art will observe that introducing the filler material 52 through one passage 70 may allow air or other gasses within the expandable member 72 to be displaced out of the second passage 71 by the incoming filler material 52. In other embodiments, the filler material 52 may be provided into both passages 70, 71 substantially simultaneously.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention is therefore not limited to the specific details, representative apparatus and process and illustrative examples shown and described. Accordingly, departures may be made from such details without departing from the scope of the general inventive concept.

What is claimed is:

1. A bone anchor system for anchoring a support member to a bone having a cavity formed therein, the system comprising:

a body having a proximal end portion, a distal end portion and a longitudinal axis extending therebetween;

a deformable member attached to the distal end portion of the body, the deformable member being deformable upon expansion from an unexpanded configuration to an expanded configuration in which the deformable member is spaced apart from the distal end portion of the body, the deformable member expanding in a radial direction;

a sleeve for attaching the deformable member to the body, the sleeve configured such that when the deformable member is placed over the body, the sleeve slides over and frictionally engages the deformable member, thereby retaining the deformable member between the body and the sleeve; and a head region at the proximal end portion of the body, the head region having a support engagement channel extending through the head in a direction transverse to the longitudinal axis, the support engagement channel configured to receive a support member.

2. The system of claim 1, further comprising a passage extending from an entry point in the head region to an exit point in the distal end portion.

3. The system of claim 2, wherein the exit point is in fluid communication with the deformable member, whereby the deformable member is adapted to expand when a filler material is provided into the entry point, passes through the passage, passes out of the exit point, and into the deformable member, thereby expanding at least a portion of the deformable member to conform to the bone cavity and anchor the system to the bone.

4. The system of claim 1, wherein the deformable member includes a flexible wall configured to conform to the bone cavity in the expanded configuration, thereby defining an anchoring chamber between the distal end portion of the body and the flexible wall.

5. The system of claim 1, further comprising a plurality of threads on the body forming a threaded portion between the proximal end portion and the distal end portion.

6. The system of claim 1, further comprising an expansion tool configured to expand the deformable member.

7. The system of claim 6, wherein the expansion tool is a cannula configured for insertion into the passage to deliver a filler material.

8. The system of claim 1, further comprising a support member releasably attached to the head region.

9. The system of claim 1, wherein the deformable member comprises a metallic fabric.

10. A bone anchor system for anchoring a support member to a bone having a cavity formed therein, the system comprising:
a body having a proximal end portion, a distal end portion and a longitudinal axis extending therebetween;
a deformable member attached to the distal end portion of the body, the deformable member being deformable upon expansion from an unexpanded configuration to an expanded configuration in which the deformable member is spaced apart from the distal end portion of the body, the deformable member expanding in a radial direction;
a sleeve for attaching the deformable member to the body, the sleeve configured such that when the deformable member is placed over the body, the sleeve slides over and frictionally engages the deformable member, thereby retaining the deformable member between the body and the sleeve; and
a head region at the proximal end portion of the body, the head region having a support engagement region adapted to receive a support member, the support engagement region configured to allow polyaxial movement of the body relative to the support member.

11. The system of claim 10, wherein the support engagement region includes a channel extending through the head region in a direction transverse to the longitudinal axis.

12. The system of claim 10, wherein the head region comprises a polyaxial top-loading head.

13. The system of claim 10, wherein the body has a passage extending from an entry point in the head region to an exit point in the distal end portion.

14. The system of claim 13, wherein the exit point is in fluid communication with the deformable member, whereby the deformable member is adapted to expand when a filler material is provided into the entry point, passes through the passage, passes out of the exit point, and into the deformable member, thereby expanding at least a portion of the deformable member to conform to the bone cavity and anchor the system to the bone.

15. The system of claim 10, wherein the deformable member includes a flexible wall configured to conform to the bone cavity in the expanded configuration.

16. A method of securing a fixation member to a bone, comprising:
preparing a hole in a portion of bone;
providing an expandable support device comprising:
a body having a proximal end portion, a distal end portion and a longitudinal axis extending therebetween;
a deformable member attached to the distal end portion of the body, the deformable member being deformable upon expansion of the expandable support device from an unexpanded configuration to an expanded configuration in which the deformable member is spaced apart from the distal end portion of the body, the deformable member expanding in a radial direction, wherein the distal end portion of the body includes a sleeve for attaching the deformable member to the body; and
a head region at the proximal end portion of the body, the head region having a support engagement channel extending through the head in a direction transverse to the longitudinal axis, the support engagement channel configured to receive a fixation member;
placing the deformable member over the distal end portion of the body, sliding the sleeve over the deformable member, whereby the sleeve frictionally engages the deformable member, thereby retaining the deformable member between the body and the sleeve;
inserting the expandable support device into the hole such that the body and deformable member are inside the hole and the head region remains outside the hole;
expanding the expandable support device within the hole; and
attaching a fixation member to the head region of the expandable support device.

17. The method of claim 16, wherein the body has a passage extending from an entry point in the head region to an exit point in the distal end portion, and the deformable member includes a flexible wall, wherein the exit point is in fluid communication with the deformable member, whereby the deformable member is adapted to expand when a filler material is provided into the entry point, passes through the passage, passes out of the exit point, and into the deformable member.

18. The method of claim 17, wherein the step of expanding the expandable support device within the hole includes inserting a filler material through the passage and into the deformable member, thereby expanding at least a portion of the deformable member to conform to the hole and anchoring the expandable support device in the hole.

* * * * *